(12) United States Patent
Siino, Jr. et al.

(10) Patent No.: US 8,975,373 B2
(45) Date of Patent: Mar. 10, 2015

(54) MULTI-PROTEIN QUANTITATION STANDARD

(71) Applicant: Bio-Rad Laboratories, Inc., Hercules, CA (US)

(72) Inventors: Joseph S. Siino, Jr., Benicia, CA (US); Dennis C. Yee, Walnut Creek, CA (US); Lee O. Lomas, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/930,059

(22) Filed: Jun. 28, 2013

(65) Prior Publication Data

US 2014/0004533 A1   Jan. 2, 2014

Related U.S. Application Data

(60) Provisional application No. 61/665,425, filed on Jun. 28, 2012.

(51) Int. Cl.
  *C07K 14/00* (2006.01)
  *G01N 33/68* (2006.01)
  *G01N 27/447* (2006.01)
(52) U.S. Cl.
  CPC .......... *G01N 33/6827* (2013.01); *G01N 27/447* (2013.01); *G01N 33/6803* (2013.01); *G01N 27/44726* (2013.01)
  USPC ........................................................ 530/350
(58) Field of Classification Search
  None
  See application file for complete search history.

(56) References Cited

U.S. PATENT DOCUMENTS

| 7,265,206 | B2 | 9/2007 | Chatterjee et al. |
| 7,569,130 | B2 | 8/2009 | Edwards et al. |
| 8,007,646 | B2 | 8/2011 | Edwards et al. |
| 2003/0157720 | A1 | 8/2003 | Li |
| 2009/0178926 | A1 | 7/2009 | Bogoev et al. |
| 2011/0108420 | A1 | 5/2011 | Chatterjee et al. |

FOREIGN PATENT DOCUMENTS

| WO | 99-58050 A1 | 11/1999 |
| WO | 03-067232 A1 | 8/2003 |
| WO | 2011-031497 A2 | 3/2011 |

OTHER PUBLICATIONS

Ladner et al., "Visible Fluorescent Detection of Proteins in Polyacrylamide Gels Without Staining", Analytical Biochemistry, 2004, vol. 326, No. 1, pp. 13-20.
International Search Report and Written Opinion mailed on Nov. 29, 2013 for International Patent Application No. PCT/US2013/048443, 10 pages.

*Primary Examiner* — Suzanne M Noakes
(74) *Attorney, Agent, or Firm* — Kilpatrick Townsend & Stockton LLP

(57) ABSTRACT

Provided is a protein quantitation standard having polypeptides of different molecular weights that functions as a mass quantitation standard in one lane of an electrophoretic gel. The protein quantitation standard includes unstained polypeptides having different electrophoretic mobilities that are present in different quantities, such that the bands in the gel have different intensities when visualized. The protein quantitation standard can also contain prestained polypeptides that function as visual molecular weight markers. Also provided are methods of determining the mass of a target polypeptide or protein using the protein quantitation standard.

20 Claims, 4 Drawing Sheets

Figure 2.

MULTI-PROTEIN QUANTITATION STANDARD

CROSS-REFERENCE TO RELATED PATENT APPLICATIONS

The present application claims benefit of priority to U.S. Provisional Patent Application No. 61/665,425, filed Jun. 28, 2012, which is incorporated by reference herein in its entirety.

FIELD OF THE INVENTION

This invention resides in the field of protein detection, in particular the quantitation of the amount of a protein in gel electrophoresis.

BACKGROUND

Gel electrophoresis, including polyacrylamide gel electrophoresis (PAGE), is a common laboratory technique for estimating the molecular weight of proteins and polypeptides. Gel electrophoresis is used to separate proteins based on their charge, size and/or molecular weight. Under non-denaturing conditions, proteins can be separated based on their charge-to-mass ratio, and the electrophoretic mobility is influenced by the size and shape of the native protein. Under denaturing conditions, for example, in the presence of an anionic detergent such as sodium dodecyl sulphate (SDS), proteins can be separated based on their molecular weights. The anionic detergent both unfolds the protein and provides a uniform negative charge density such that the electrophoretic mobility of the protein is a linear function of the logarithm of the molecular weight.

Methods for quantifying the amount of a protein in a sample are known in the art, including the Bradford assay. The Bradford assay relies on a standard curve generated from known protein standards to determine the total amount of the unknown protein. However, the Bradford assay is typically performed using solutions containing the protein of interest. Purified protein quantity can be measured using spectrophotometric methods if an extinction coefficient is known for the protein of interest. The quantity of a protein can also be determined by mass spectrometry coupled with isotope-labeling methods (e.g., ICAT, iTRAQ, and Tandem Mass Tags). However, spectrophotometric methods are limited to measurements of pure protein in solution. Current methods for quantifying a protein on SDS-PAGE gels involve generating a standard curve from a dilution series of known masses of a purified protein, where each dilution is subjected to electrophoresis in a separate lane of the gel in parallel with the sample containing the target protein of interest.

The present disclosure describes a protein quantitation standard that is useful for quantifying the amount of a protein in an electrophoresis gel, and methods for determining the quantity of a protein in a gel that do not require generating a dilution series of a known protein mass or preparing purified samples of the protein of interest.

SUMMARY OF THE DISCLOSURE

The present disclosure describes a protein quantitation standard that can be used to determine the mass (i.e., the amount or quantity) of a target protein in an electrophoresis gel. The standard comprises a set of unstained polypeptides that can be used to generate a mass standard curve for determining the amount of the target polypeptide in the gel. The set of unstained polypeptides can be provided in a mixture that is suitable for loading and electrophoretically separating in one lane of a gel. The protein quantitation standard can also include a set of prestained polypeptides that can be used as a molecular weight ladder for determining the molecular weight (i.e., the size) of a target polypeptide. Thus, in some embodiments, the protein quantitation standard can be used to determine both the molecular weight and the mass of a target protein in an electrophoresis gel. The set of prestained polypeptides and the set of unstained polypeptides can be provided in a mixture that is suitable for loading and electrophoretically separating in one lane of a gel. When electrophoretically separated, the prestained polypeptides appear as bands on a gel, and allow the user to determine the extent of separation between polypeptides of different sizes. The target protein is typically loaded and electrophoretically separated in another lane of the gel.

Thus, in one aspect, a protein quantification standard that can be loaded into one lane of an electrophoresis gel is provided, the standard comprising a set of unstained polypeptides, wherein members of the set of unstained polypeptides have different electrophoretic mobilities and are present in different quantities, such that the standard is suitable for generating a protein mass standard curve from one lane of a gel. In one embodiment, different members of the set of unstained polypeptides have different molecular weights and/or different electrophoretic mobilities. In one embodiment, each member of the set of unstained polypeptides has a different molecular weight and/or different electrophoretic mobility than other members of the set of unstained polypeptides.

In some embodiments, the protein quantification standard further comprises a set of prestained polypeptides having different molecular weights and/or different electrophoretic mobilities, such that the standard is suitable for generating a molecular weight ladder and a protein mass standard in one lane of a gel. In one embodiment, different members of the set of prestained polypeptides have different molecular weights and/or different electrophoretic mobilities. In one embodiment, each member of the set of prestained polypeptides has a different molecular weight and/or different electrophoretic mobility than other members of the set of prestained polypeptides. In some embodiments, at least one prestained polypeptide and at least one unstained polypeptide of the standard have different electrophoretic mobilities.

In some embodiments, the protein quantification standard comprises a set of prestained polypeptides having different molecular weights and a set of unstained polypeptides having different molecular weights in a common mixture, wherein members of the set of unstained polypeptides have different electrophoretic mobilities and are present in different quantities, such that the standard is suitable for generating a molecular weight ladder and a protein mass standard in one lane of an electrophoresis gel. The protein mass standard can be used to generate a protein mass standard curve from one lane of a gel.

In another embodiment, methods are disclosed for determining the mass quantity or amount of a target protein. Thus, in some embodiments, the method comprises electrophoretically migrating the target polypeptide in one lane of a gel and a protein quantitation standard in another lane of a gel, where the protein quantitation standard comprises a set of unstained polypeptides having different electrophoretic mobilities that are present in different quantities; detecting the target polypeptide and the protein quantitation standard; and comparing the detected amount of the target polypeptide to a mass standard curve generated from the protein quantitation standard in order to determine the mass quantity of the target protein. In some embodiments, the method comprises visually comparing the amount of the target polypeptide in the gel to the bands of the protein quantitation standard in the gel, or an image of the gel, in order to determine or estimate the mass quantity or amount of the target polypeptide. The method can also detect a protein standard comprising prestained polypeptides that are useful for determining the apparent molecular weight of the target protein. The unstained polypeptides can be visualized or detected during or after the gel separation is complete, as described in more detail herein. In some embodiments, the detecting comprises stain-free imaging. In some embodiments, the detecting comprises fluorescence imaging. In some embodiments, the detecting comprises contacting the unstained polypeptides with a stain or dye and visualizing the polypeptides. The methods can be practiced on a denaturing gel, such as an SDS-PAGE gel, or on a non-denaturing gel.

In some embodiments, the method further comprises contacting the unstained polypeptides with one or more ligands that specifically bind the polypeptides of the standard. In some embodiments, the one or more ligands are conjugated with a chromogenic or chemiluminescent reagent.

The disclosure further provides methods for determining the mass of a target protein in a microfluidic electrophoresis instrument or capillary electrophoresis instrument. Thus, in some embodiments, a method of determining the mass quantity of a target polypeptide is described, the method comprising:

electrophoretically migrating the target polypeptide and the protein quantitation standard described herein in a microfluidic instrument;

detecting the target polypeptide and the protein quantitation standard; and comparing the detected amount of the target polypeptide to a mass standard curve generated from the protein quantitation standard to thereby determine the mass quantity of the target polypeptide.

The disclosure also provides a computer implemented method for determining the mass or amount of a target protein. The computer implemented method can be performed using a gel or image of a gel that has been subjected to electrophoretic separation of the protein standard. In some embodiments, the computer implemented method comprises:

quantifying the unstained polypeptides in a protein quantitation standard, the protein quantitation standard comprising a set of unstained polypeptides having different electrophoretic mobilities present in different quantities;

generating a regression fit based on the quantifying step;

calculating the target polypeptide's mass from the regression fit; and providing the calculated mass.

The regression fit can be a linear or non-linear regression. In some embodiments, the computer implemented method is under the control of one or more computer systems configured with executable instructions.

In another aspect, a computer product for performing one or more steps of the methods described herein is described. In one embodiment, the computer product comprises a non-transitory computer readable medium storing a plurality of instructions for controlling a processor to perform an operation of one or more of the following steps:

(i) receiving data comprising the quantity of the unstained polypeptides in a protein quantitation standard, the protein quantitation standard comprising a set of unstained polypeptides having different electrophoretic mobilities present in different quantities;

(ii) generating a regression fit based on the data received;

(iii) calculating the target polypeptide's mass from the regression fit; and (iv) providing the calculated mass.

In some embodiments, a computer system is provided that comprises a computer product for performing one or more steps of the methods described herein. In one embodiment, the computer system comprises a non-transitory computer readable medium storing a plurality of instructions for controlling a processor to perform an operation of one or more of the following steps:

(i) receiving data comprising the quantity of the unstained polypeptides in a protein quantitation standard, the protein quantitation standard comprising a set of unstained polypeptides having different electrophoretic mobilities present in different quantities;

(ii) generating a regression fit based on the data received;

(iii) calculating the target polypeptide's mass from the regression fit; and (iv) providing the calculated mass; and one or more processors for executing instructions stored on the computer readable medium.

In some of the above embodiments, the regression fit is a linear regression fit. In certain embodiments, the regression fit is a non-linear regression fit.

Further embodiments are described herein.

BRIEF DESCRIPTION OF THE DRAWINGS

FIG. 2 shows a schematic of a gel or blot image showing illustrative examples of two embodiments of a multi-protein quantitation standard. The left lane ("Color") of each example shows the prestained proteins of the standard can function as a molecular weight ladder. The middle lane of each example shows the unstained polypeptides of the standard can be detected by one of several methods, including Coomassie dye, stain-free detection, or chemiluminescent detection after Western blot. The right lane ("Fluor excitation") of each example provides a representative illustration showing how the prestained proteins of the left lane would look when visualized with fluorescence excitation (fluorescent colors and patterns indicated are for illustrative purposes only). In the embodiment illustrated in Example 1, the unstained polypeptides of the standard cluster in a narrow molecular weight range between two of the bands representing prestained molecular weight marker polypeptides. Example 2 illustrates an embodiment where the unstained polypeptides of the standard are distributed between multiple bands representing prestained molecular weight marker polypeptides.

DEFINITIONS

Figure 1:
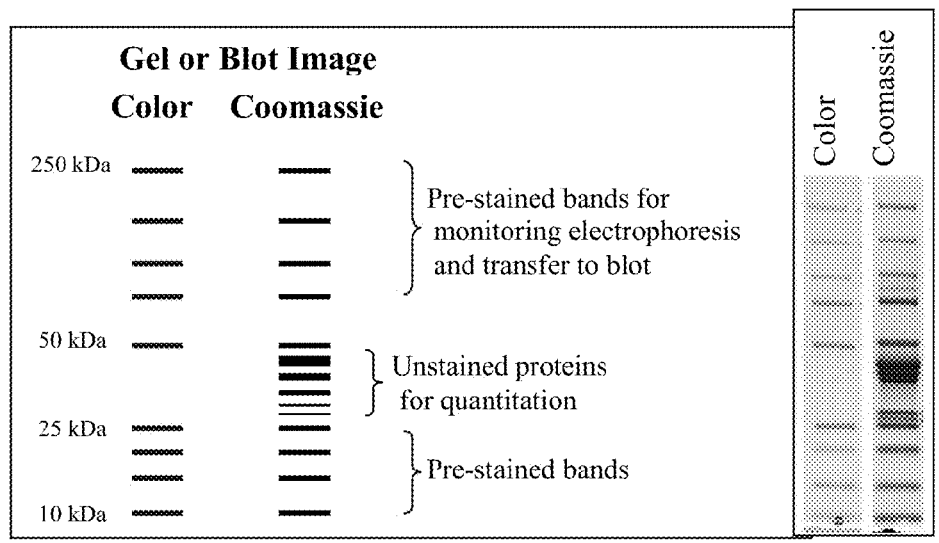
FIG. 1 shows a schematic of a gel or blot image showing illustrative examples of one embodiment of the protein quantitation standard. Left panel: bands corresponding to the prestained polypeptides are shown in color in the left lane and bands corresponding to Coomassie stained polypeptides are shown in the right lane. Right panel: An actual gel image showing prestained bands of the standard in the left lane, and Coomassie stained bands of the standard in the right lane.

As used herein, the term "prestained polypeptide" refers to a polypeptide that is labeled or conjugated to a dye or stain.

For example, the polypeptide can be labeled with blue or pink dyes to provide color landmarks as the polypeptide migrates in the gel.

As used herein, the term "stain-free imaging" refers to a method for visualizing proteins by means of an ultraviolet (UV) light-dependent reaction between the amino acid tryptophan (Trp) and a halo-substituted organic compound, which results in a product that fluoresces in the visible light range. Examples of stain free imaging are described in U.S. Pat. Nos. 7,569,130 and 8,007,646, which are incorporated by reference herein in their entirety.

As used herein, the term "chemiluminescence" refers to the emission of energy with limited emission of heat due to a chemical reaction. The term "enhanced chemiluminescence" refers to the use of an enzyme (e.g., HRP) to catalyze the conversion of a chemiluminescence substrate into a sensitized reagent. The sensitized reagent can be oxidized, e.g., by hydrogen peroxide, which produces a triplet carbonyl that emits light when it decays to the singlet carbonyl. The term "chemiluminescent reagent" refers to a molecule or enzyme that catalyzes the conversion of a chemiluminescence substrate into a sensitized reagent.

The term "mass quantity" of a polypeptide refers to the absolute amount of a given protein in a sample. The mass quantity can be expressed in terms of the number of micrograms of a protein or polypeptide in a sample, for example, the number of micrograms of a target protein loaded into one lane of an electrophoresis gel.

The term "label" or "detectable moiety" is used herein to denote a composition detectable by spectroscopic, photochemical, biochemical, immunochemical, chemical, or other physical means. Examples of labels are $^{32}P$, fluorescent dyes, electron-dense reagents, enzymes (e.g., as commonly used in an ELISA), biotin, digoxigenin, and haptens and proteins or other entities which can be made detectable, e.g., by incorporating a radiolabel into the peptide or by being used to detect antibodies specifically reactive with the peptide. The labels can be incorporated, for example, into antibodies and/or other proteins at any position. Any method known in the art for conjugating the antibody to the label can be employed, for example, using methods described in Hermanson, *Bioconjugate Techniques* 1996, Academic Press, Inc., San Diego. Alternatively, methods using high affinity interactions can achieve the same results where one of a pair of binding partners binds to the other, e.g., biotin and streptavidin. The proteins described herein can be directly labeled as with isotopes, chromophores, lumiphores, chromogens, or indirectly labeled such as with biotin to which streptavidin in a complex with a fluorescent, radioactive, or other moiety that can be directly detected can then bind. Thus, a biotinylated antibody is considered a "labeled antibody" as used herein.

The term "antibody" as used herein refers to a polypeptide encoded by an immunoglobulin gene or immunoglobulin genes, or fragments thereof, which specifically bind and recognize an antigen, for example, a polypeptide of the standard or a peptide tag that is part of a fusion protein of the standard. The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

The expression "specifically (or selectively)" in reference to binding to an antibody or ligand, or "specifically (or selectively) immunoreactive with" or "having binding specificity for," when referring to a protein, peptide, or antigen, refers to a binding reaction which is determinative of the presence of the protein, peptide, or antigen in the presence of a heterogeneous population of proteins and other biologics. Thus, under designated conditions, the specified antibodies bind to a particular protein and do not bind in a significant amount to other proteins present in the sample or the protein standard. Specific binding to an antibody under such conditions may require an antibody that is selected for its specificity for a particular protein. For example, antibodies raised against a protein can be selected to obtain antibodies specifically immunoreactive with that protein and not with other proteins. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane Antibodies, A Laboratory Manual, Cold Spring Harbor Publications, NY (1988) for a description of immunoassay formats and conditions that can be used to determine specific immunoreactivity. Typically, a specific or selective reaction will be at least twice the background signal or noise, and more typically more than 10 to 100 times background.

The term "solid support" is used herein to denote a solid inert surface or body to which an agent, such as a protein or polypeptide, can be immobilized. The term "immobilized" as used herein denotes a molecularly based coupling that is not dislodged or de-coupled under any of the conditions imposed during any of the steps of the assays described herein. Such immobilization can be achieved through a covalent bond, an ionic bond, an affinity-type bond, or any other chemical bond.

The terms "polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds. The polypeptide can be natural or recombinant, and may contain natural or non-natural amino acids. The protein can be a fusion protein that contains amino acids from heterologous proteins or polypeptides, or contains artificial peptides added to the amino (N) or carboxyl (C) terminus of the protein.

The term "fusion protein" refers to a polypeptide comprising amino acids from two or more heterologous or different peptides or polypeptides that are joined by peptide bonds. A fusion protein can be produced from a recombinant nucleic acid molecule that encodes the two or more heterologous peptides or polypeptides such that the polypeptides are joined in frame. The phrase "joined in frame" refers to joining two or more polynucleotide sequences that encode polypeptides so that the joined nucleic acid sequence translates into a single chain polypeptide comprising the original polypeptides fused together. The fusion protein can also be produced by peptide synthesis of the desired amino acid sequence.

The term "ligand" refers to a compound or molecule that specifically and reversibly binds to another chemical entity, compound, or polypeptide to form a complex.

The terms molecular weight ladder and molecular weight marker are used interchangeably, and refer to polypeptides that, when electrophoretically separated, appear as bands of known size on a gel.

Description of Selected Embodiments

The present disclosure provides a protein quantitation standard that is useful for quantifying the amount or mass of a polypeptide of interest (sometimes referred to herein as a target protein or target polypeptide) in a sample, for example, in gel electrophoresis. In some embodiments, the protein quantitation standard is also useful as a molecular weight marker in gel electrophoresis. The protein quantitation standard can thus have a dual function as both a mass quantitation standard and a molecular weight marker in a single lane of a gel electrophoresis apparatus. The disclosure further provides kits comprising the protein quantitation standard described herein. The disclosure also provides methods, including computer implemented methods, of determining the mass quantity of a target polypeptide in a sample. The methods can further determine both the mass quantity and the size of a target protein. The target polypeptide can be a known or unknown polypeptide.

I. The Protein Quantitation Standard

The disclosure provides a protein quantitation standard comprising a plurality of polypeptides having different electrophoretic mobilities and different mass quantities that is suitable for generating a protein mass standard in one lane of a gel. The protein quantitation standard can be used to generate a protein mass standard curve from one lane of a gel. Current methods for quantifying a protein on SDS-PAGE gels involve generating a standard curve from a dilution series of known amounts of a purified protein, where each dilution is subjected to electrophoresis in a separate lane of the gel in parallel with the sample containing the target protein of interest. The current methods therefore use multiple lanes of a gel to generate a standard curve (e.g., 3 to 5 lanes or more, depending on the number of points desired to generate the standard curve), which leaves fewer lanes available for loading target proteins of interest. Thus, using current methods, a substantial fraction of the lanes on the gel is unavailable for analyzing the protein of interest. The inventors have unexpectedly discovered that by using different amounts of polypeptides having different electrophoretic mobilities (or different apparent molecular weights), a standard curve can be generated from one lane of a gel.

In some embodiments, the protein quantitation standard comprises a set of unstained polypeptides, where members of the set of unstained polypeptides have different electrophoretic mobilities and are present in different mass quantities. In some embodiments, the protein quantitation standard comprises a set of prestained polypeptides, where members of the set of prestained polypeptides have different electrophoretic mobilities and/or different molecular weights. In some embodiments, the protein quantitation standard comprises a mixture of prestained polypeptides and unstained polypeptides. In some embodiments, the standard comprises a set of prestained polypeptides having different molecular weights and a set of unstained polypeptides having different molecular weights, wherein members of the set of unstained polypeptides have different electrophoretic mobilities and are present in different mass quantities, such that the standard is suitable for generating a molecular weight ladder and a protein mass standard in one lane of a gel. For example, in some embodiments, each member of the set of unstained polypeptides has a different electrophoretic mobility and is present in a different quantity, such that, after electrophoretic separation, each band on the gel has a different intensity when visualized or detected. The polypeptides can be natural or recombinant proteins. In some embodiments, the polypeptides are fusion proteins.

A. Prestained Polypeptides of the Standard

The prestained polypeptides of the standard can be used as a molecular weight ladder or markers in gel electrophoresis, where the polypeptides appear as bands in the gel matrix when separated by gel electrophoresis. In some embodiments, the prestained polypeptides are labeled with one or more colored dyes. The one or more colored dyes can also be fluorescent dyes. The prestained polypeptides allow a user to, for example, visually monitor the progress of the electrophoresis, or to visually monitor transfer of the gel to a solid support without having to stain the gel with a dye such as Coomassie blue. All of the prestained polypeptides can be stained with the same color dye or some of the prestained polypeptides can be stained with different color dyes and/or different fluorescent dyes to allow the user to more easily distinguish polypeptides having different molecular weights. In some embodiments, the one or more colored dyes comprise a single color dye. In one embodiment, the one or more colored dyes comprise a combination of different colored dyes. For example, some of the polypeptides in the standard can be stained pink to serve as reference bands of known molecular weight (e.g., 25, 50 and 75 kDa), whereas the other polypeptides in the standard can be stained blue. The stains used can be commercially available protein stains and dyes that are readily available to one of skill in the art. For example, the protein binding dye can be any dye that binds covalently to the polypeptides. In some embodiments, the dye is visible to the human eye, for example a chromophore. Methods for conjugating a dye to a protein, for example, to the amino group of lysine residues, the N-terminus of the protein, histidine, tryptophan; the sulfhydryl group of cysteine; the carboxyl group of aspartate and glutamate; the thioether of methionine, and the phenolate of tyrosine are well known in the art (see, for example, Hermanson, Bioconjugate Techniques, Academic Press, San Diego (1996); Wong, Chemistry of Protein Conjugation and Cross-Linking, CRC Press, Boca Raton, 1993; Haugland, MOLECULAR PROBES HANDBOOK (2002)). Examples of methods for staining polypeptides are provided in U.S. Pat. No. 7,265,206, which is incorporated herein by reference in its entirety. In some embodiments, the prestained polypeptides are labeled with fluorescent dyes. In some embodiments, the set of prestained polypeptides are labeled with a combination of colored dyes and fluorescent dyes. In one embodiment, each member of the set of prestained polypeptides can be labeled with a different colored dye or different fluorescent dye. In some embodiments, the prestained polypeptides produce bands on a gel that appear to have similar staining intensities when visualized or detected.

In some embodiments, the prestained polypeptides of the standard have different molecular weights but similar mass quantities. In other words, one or more of the prestained polypeptides have different apparent sizes when separated on a gel, but appear to have similar amounts of protein in one or more bands of the gel. In some embodiments, the prestained polypeptides of the standard have different molecular weights and different mass quantities, such that when separated on a gel, one or more of the prestained polypeptides appear to have a different amount of protein in one or more bands of the gel.

In some embodiments, the prestained polypeptides of the standard range in size from about 2 kDa to about 250 kDa. In some embodiments, the prestained polypeptides range in size from about 2 kDa to about 500 kDa. It will be understood that, as used herein, a range can include the endpoints and all points in between. For example, the prestained polypeptides can be about 2 kDa, 5 kDa, 10 kDa, 15 kDa, 20 kDa, 25 kDa, 37 kDa, 50 kDa, 75 kDa, 100 kDa, 150 kDa, and 250 kDa. The standard can include a mixture of prestained polypeptides that range in size from about 2 kDa to about 500 kDa.

In some embodiments, the standard comprises at least two, three, four, five, six, seven, eight, nine, ten or more prestained polypeptides having different molecular weights and/or different electrophoretic mobilities.

In some embodiments, the prestained polypeptides can be visualized or detected using stain-free imaging. For example, the stain-free imaging can make use of a halo-substituted organic compound. When exposed to UV irradiation, the halo-substituted organic compound covalently reacts with tryptophan residues in the polypeptide to form compounds which fluoresce when illuminated with UV light, for example from a UV transilluminator. For example, the polypeptides can be illuminated with UV light in the range of about 280 nm to about 320 nm. The fluorescent polypeptides can be visualized by the naked eye or by using imaging devices. The halo-substituted organic compound can be incorporated into the gel either prior to electrophoresis or after electrophoresis. A variety of halo-substituted organic compounds can be used in the embodiments described herein, indeed any of halo-substituted organic compounds can be used that will enter into a chemical reaction with tryptophan to form a product that fluoresces upon exposure to excitation light. Halo-substituted organic compounds of particular interest are trihalo compounds, most notably trichloro compounds and those with molecular weights of 200 or less. Trihaloaliphatic alcohols, trihaloaliphatic acids, trihaloaliphatic amines, and trihaloalkanes are all useful. Specific examples are chloroform, trichloroacetic acid, and trichloroethanol. Halo-substituted organic compounds can be used individually or in combinations, such as for example combinations of two or three such compounds in approximately equal molar proportions. Methods of detecting proteins using stain-free imaging are described in U.S. Pat. Nos. 7,569,130 and 8,007,646, which are incorporated by reference herein in their entirety.

In some embodiments, the prestained polypeptides can be visualized or detected using fluorescence imaging. For example, in some embodiments, polypeptides that are colored blue appear as red bands when illuminated with the appropriate wavelength (e.g., where the polypeptide is labeled with UNIBLUE A™, a blue dye, excitation with red light produces a further red-shifted fluorescence). In some embodiments, polypeptides that are colored red appear as yellow bands when illuminated with the appropriate wavelength (e.g., where the polypeptide is labeled with TRITC, a red dye, excitation with green light produces a yellowish fluorescence). Visualization of the prestained polypeptides by fluorescence imaging can be accomplished by using UV light excitation sources in the range of about 280 nm to about 320 nm. In some embodiments, the prestained polypeptides can be illuminated using an excitation source such as laser light or LED light in a narrow wavelength range, for example about 488 nm (blue), about 555 nm (green), or about 630 nm (red). As is understood by those of skill in the art, the fluorescence emission spectra from the excitation wavelengths is of longer wavelength than the excitation wavelength, and the emission spectra can be detected after filtering out the light near and below the excitation wavelength. For example, in some embodiments, the excitation wavelength is filtered using 530 nm, 605 nm, and/or 695 nm band pass filters. However, it will be understood that the choice of suitable filters will depend on the excitation and emission characteristics of the protein dye or stain. In some embodiments, the dye used to pre-stain the polypeptides will have strong fluorescent excitation at both short wavelengths (UV) (e.g., from a UV transilluminator) and longer wavelengths, for example green light at about 555 nm or red light at about 630 nm, and will emit fluorescence energy at an even longer wavelength, for example at about 576 nm for excitation with green light. In some embodiments, the dye will have a bright color in wavelengths visible to the human eye but attenuated signal when viewed using fluorescent imaging.

In some embodiments, the prestained polypeptides can be visualized using near-infrared imaging. For example, the polypeptides that are labeled with dyes as described herein can be excited with 650-800 nm wavelength energy, and the excited dyes will emit energy at wavelengths of about 670-820 nm.

B. The Unstained Polypeptides of the Standard

The unstained polypeptides of the quantitation standard are useful for quantifying the amount or mass of a target polypeptide. For example, in some embodiments, the unstained polypeptides can be used to visually estimate the mass quantity of a target polypeptide after staining the gel with a dye such as Coomassie blue. In some embodiments, the unstained polypeptides can be used to generate a standard curve using known protein mass quantities for one or more of the unstained polypeptides in the standard. In some embodiments, the standard comprises a plurality or set of unstained polypeptides having different molecular weights, where the unstained polypeptides having the same molecular weight have a different mass quantity than the other unstained polypeptides in the standard. Thus, the amount of one or more unstained polypeptides having the same size in the standard can differ from the amount of the other unstained polypeptides having different sizes in the standard. For example, the mass quantity of a first unstained polypeptide having a first molecular weight can differ from the mass quantity of a second unstained polypeptide having a second molecular weight. The amount of each unstained polypeptide can be selected to generate a standard mass curve that encompasses the expected mass of a target protein of interest. The amount of each unstained polypeptide used to generate the standard curve can be determined, for example, by densitometry scanning the bands in the gel lane.

In some embodiments, the unstained polypeptides can be visualized or detected using stain-free imaging, as described above. In some embodiments, the unstained polypeptides can be used to measure protein quantity using stain-free imaging of the band intensity in the gel. In some embodiments, the unstained polypeptides can be used to measure protein quantity using stain-free imaging of the band intensity after the gel has been transferred to a solid support. Examples of solid supports are well known in the art, and include nitrocellulose or polyvinylidene difluoride (PVDF) membranes.

In some embodiments, the unstained polypeptides can be visualized using near-infrared imaging, as described above. For example, the unstained polypeptides can be stained with an appropriate dye, such as Coomassie, and visualized using near-infrared imaging. The unstained polypeptides can also be transferred to a solid support (e.g., a nylon membrane as in a Western blot), contacted with a suitable antibody-dye or protein-dye conjugate, and visualized using near-infrared imaging.

The unstained polypeptides can also be visualized in the gel matrix or after transfer to a solid support using fluorescent stains such as SYPRO® Ruby (Life Technologies) or Flamingo™ stain (Bio-Rad). In some embodiments, the unstained polypeptides can be visualized in the gel matrix while electrophoresis is in progress, using one or more of the visualization methods described herein.

In some embodiments, the unstained polypeptides can be detected by contacting the unstained polypeptides with an antibody or ligand having high affinity or high specificity for the unstained polypeptides. The antibody or ligand can be labeled or conjugated with a detectable moiety, such as a fluorescent dye, or chromogenic or chemiluminescent reagent In some embodiments, the unstained polypeptides comprise fusion proteins that include affinity tags. Examples of affinity tags include N-terminal or C-terminal polyhistidine-tags that allow affinity purification of the polypeptides by binding to columns or resins containing bound metal ions, such as nickel of cobalt. The affinity tags can also comprise other short amino acid peptides that bind to streptavidin, engineered versions of streptavidin (e.g., StrepTag® II), or other ligands.

The unstained polypeptides can also comprise fusion proteins that include chromogenic and/or chemiluminescent detection tags. For example, the polypeptides of the standard can be recombinantly produced as fusion proteins that contain a short amino acid sequence that functions as a detection tag. In some embodiments, the detection tag is contacted with an antibody that specifically binds the detection tag but does not bind other proteins in the sample. In some embodiments, the antibody that binds the detection tag is directly coupled to an enzyme that can be used to produce a chromogenic or chemiluminescent reaction. In some embodiments, the enzyme is alkaline phosphatase (AP) for chromogenic or chemiluminescent detection or HRP for chemiluminescent detection. If AP is used, the tagged polypeptide can be detected using the chromogenic substrate p-nitrophenyl phosphate, which yields a soluble product detectable at 405 nm. For chemiluminescent detection, the HRP enzyme can be incubated with the substrate luminol and optionally an enhancer. If HRP is used, the tagged polypeptide can also be detected using the chromogenic substrate tetramethylbenzidine (TMB), which yields a soluble product in the presence of hydrogen peroxide that is detectable at 450 nm. In some embodiments, the affinity tag can also serve as a detection tag. For example, a polyhistidine tag can bind a Ni-NTA-alkaline phosphatase conjugate, which is then incubated with nitroblue tetrazolium chloride (NBT)/5-bromo-4-chloro-3-indolylphosphate p-toluidine salt (BCIP) to detect the polypeptide in a Western Blot (see Hochuli, E., and Piesecki, S., Methods: A Companion to Methods in Enzymology 4:68-72 (1992)).

In some embodiments, the antibody that binds the detection tag is contacted with a secondary antibody that is coupled to an enzyme that can be used to produce a chromogenic or chemiluminescent reaction. In some embodiments, the detection tag is capable of binding to streptavidin or an engineered streptavidin. For example, in some embodiments, the fusion protein containing the detection tag is contacted with an engineered streptavidin that is conjugated to HRP (e.g., StepTactin®-HRP). The polypeptides can also comprise fusion proteins that include peptide sequences that specifically bind IgG antibodies. In these embodiments, the user can detect the polypeptides of the standard using the same primary and secondary antibodies used for the chemiluminescent detection of proteins in the sample that are loaded into the gel.

In some embodiments, the unstained polypeptides comprise the amino acid tryptophan (Trp or W) for improved stain-free quantitation. For example, the unstained polypeptides can be selected or engineered to have specific tryptophan content for quantitation using stain-free methods described herein. In some embodiments, the unstained polypeptides comprise the same, approximately the same, or a substantially similar (e.g., no more than 5% difference) percentage of tryptophan amino acids, which allows for the amount of tryptophan to scale with the mass quantity of the polypeptide. In some embodiments, the polypeptides are engineered to have an average tryptophan content that matches the average tryptophan content of the proteins in the sample loaded onto the gel. In some embodiments, the tryptophan content is about 1.5% to about 2.5% of the polypeptides in the standard (i.e., about 1.5% to about 2.5% of the amino acids in each polypeptide of the standard are tryptophan).

Figure 2:
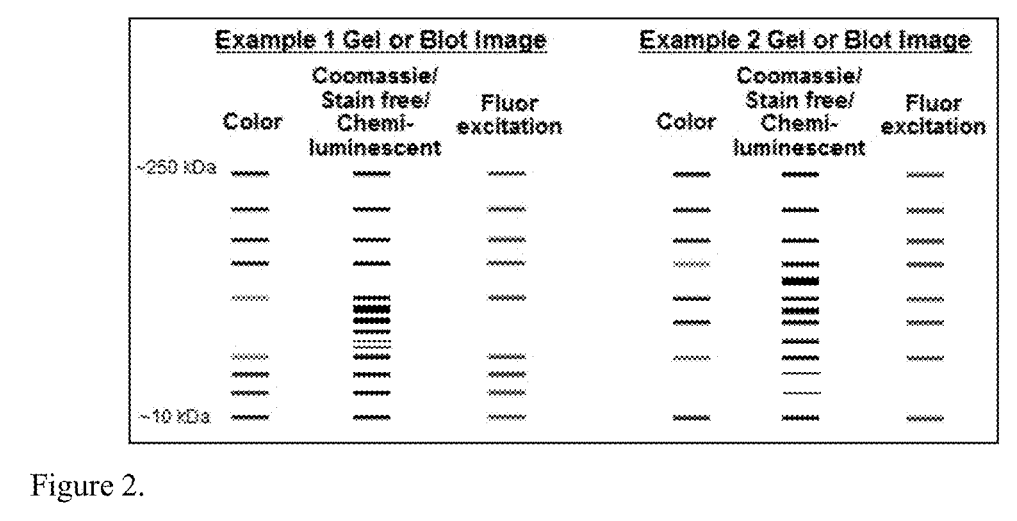

In some embodiments, the size of the unstained polypeptides is selected such that the molecular weights of the unstained polypeptides are focused in a relatively narrow range when subjected to gel electrophoresis. For example, as shown in FIG. 2 (Example 1), in one embodiment the unstained polypeptides have molecular weights that fall between the molecular weights of two consecutive prestained polypeptides of the molecular weight ladder. In some embodiments, the unstained polypeptides are selected to be in the size range of a target protein of interest that is in the sample loaded onto the gel. For example, the molecular weights of the individual unstained polypeptides are selected to flank the molecular weight of the target protein of interest, such that some of the unstained polypeptides have a molecular weight that is less than that of the target protein, whereas some of the unstained polypeptides have a molecular weight that is greater than that of the target protein.

In other embodiments, the size of the unstained polypeptides is selected such that the molecular weights of the individual polypeptides are distributed or dispersed between the molecular weights of the prestained polypeptides. For example, as shown in FIG. 2 (Example 2), in one embodiment the unstained polypeptide bands are distributed between multiple prestained polypeptide bands of the molecular weight ladder when subjected to gel electrophoresis. In one embodiment, an unstained polypeptide is flanked by two prestained polypeptides in the gel. Thus, in some embodiments, the molecular weight of one member of the set of unstained polypeptides is less than the molecular weight of a first prestained polypeptide and greater than the molecular weight of a second prestained polypeptide. In some embodiments, the unstained polypeptides range in size from about 2 kDa to about 500 kDa, about 2 kDa to about 250 kDa, about 2 kDa to about 100 kDa, about 20 kDa to about 100 kDa, or from about 20 kDa to about 50 kDa.

In some embodiments, the standard comprises at least two, three, four, five, six, seven, eight, nine, ten or more unstained polypeptides having different molecular weights and/or different electrophoretic mobilities.

In some embodiments, the protein quantitation standard comprises unlabeled or unstained versions of the prestained polypeptides (i.e., unstained polypeptides having the same amino acid sequence as the prestained polypeptides). In one embodiment, the protein quantitation standard comprises a mixture of the unstained and prestained versions of the same polypeptides. In some embodiments, the prestained polypeptide exhibits the same apparent molecular weight or migration in the gel as an unstained polypeptide having the same amino acid sequence.

II. Methods

Also provided are methods of determining the mass quantity of a target polypeptide. In one example of the methods, a sample containing a target protein or polypeptide and the protein quantitation standard are subjected to gel electrophoresis to separate the polypeptides by size, charge and/or shape. In some embodiments, the polypeptides are electrophoretically separated in a denaturing gel. For example, in one embodiment, the polypeptides are electrophoretically separated in an SDS-PAGE gel. In some embodiments, the polypeptides are electrophoretically separated in a non-denaturing gel (i.e., native gel electrophoresis). For example, in one embodiment, the polypeptides are electrophoretically separated in a polyacrylamide gel without SDS. The polypeptides can be electrophoretically separated in a Tris-Glycine gel with or without SDS. In some embodiments, the target protein and the protein quantitation standard are electrophoretically migrated in different lanes of the gel. In some embodiments, the standard comprises a set of unstained polypeptides having different electrophoretic mobilities and different quantities. In some embodiments, the standard comprises a set of prestained polypeptides that can be used to visually monitor the migration of the polypeptide bands as electrophoresis proceeds and the polypeptides migrate within the gel matrix. Thus, in some embodiments, the method further comprises detecting prestained polypeptide bands of a protein standard to determine the apparent molecular weight of the target protein. The prestained polypeptides can be included with the unstained polypeptides in the protein quantitation standard, or can be provided in a separate molecular weight standard as is well known in the art.

Figure 3:
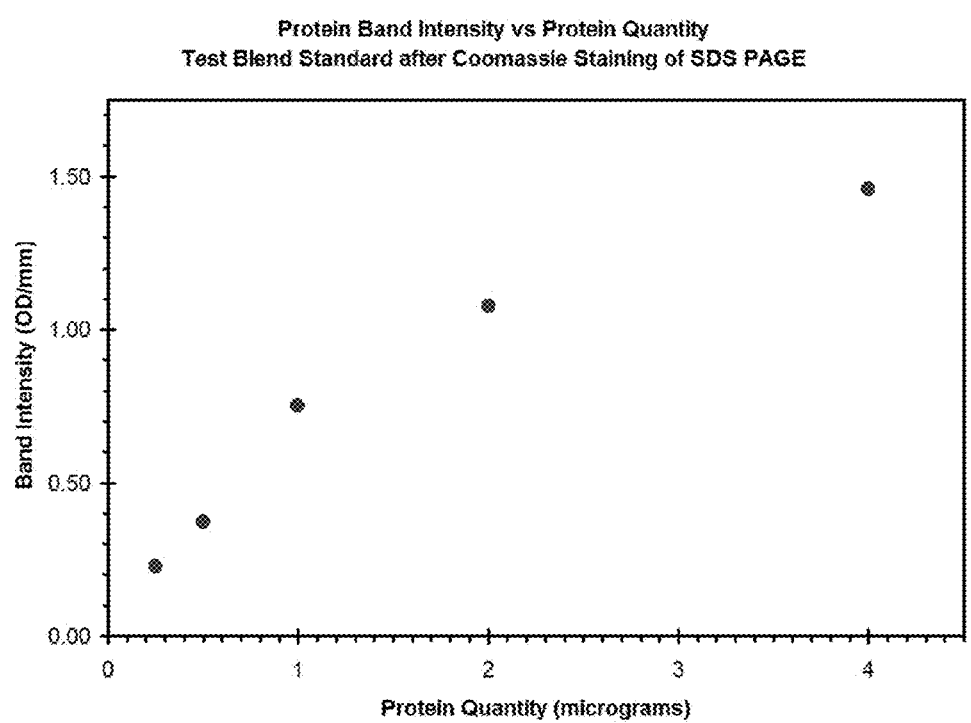
FIG. 3 shows an representative standard curve for the protein standard shown in the gel image of FIG. 1.

After the polypeptides of the standard are determined to be sufficiently separated in the gel, the unstained polypeptides of the standard can be stained. For example, the unstained polypeptides can be stained with a dye such as Coomassie. In some embodiments, the unstained polypeptides comprise a known mass quantity for each polypeptide that can be used to generate a standard curve for quantifying the mass of a target protein. In some embodiments, the standard curve is generated by densitometry measurements of the bands that correspond to the unstained polypeptides of the standard. The quantitation standard can also be used to generate a standard curve for estimating the size of a target protein based on its molecular weight. A representative gel showing the protein standard stained with Coomassie is shown in FIG. 1. A standard curve generated from the gel image in FIG. 1 is shown in FIG. 3. To determine the amount of a target protein loaded on the same gel, the user can visually estimate the unknown target protein quantity by comparing it to the band intensity of the protein standard in the gel or on the standard curve, or, alternatively, fit a line to the standard curve and calculate the unknown protein amount based on the measured band intensity. In other embodiments, the prestained polypeptides comprise a known mass quantity for each polypeptide that can be used to generate a standard curve for quantifying the mass of a target protein.

In some embodiments, the mass quantity of a target polypeptide is determined by generating a standard curve based on quantifying the unstained polypeptides of the standard using stain-free imaging of the polypeptide bands in the gel. In some embodiments, the mass quantity of a target polypeptide is determined by generating a standard curve based on quantifying the unstained polypeptides using a Western blot. For example, polypeptides in the gel can be transferred to a solid support and detected by contacting the polypeptides on the solid support with antibodies that specifically bind each polypeptide. Thus, in some embodiments, the mass quantity of a target polypeptide is determined by comparing the amount of antibody binding to the target protein with the amount of antibody binding to a known mass quantity for each polypeptide in the standard. In one embodiment, a standard curve can be generated from the band intensities in the Western blot. In some embodiments, the antibody binding is detected using a chemiluminescence assay.

In some embodiments, the methods can determine the mass of a target protein in a microfluidic electrophoresis instrument or capillary electrophoresis instrument. For example, the protein quantitation standard can be electrophoresed in a microfluidic electrophoresis instrument such as the Bio-Rad Experion™ automated electrophoresis station. In some embodiments, the automated methods can also determine the molecular weight of the target protein.

Microfluidic electrophoretic analysis utilizes a microfluidic channel filled with a polymerized gel to separate denatured proteins by size. In a typical microfluidic electrophoretic assay, a reference sample is run that contains a set of unstained molecular weight markers that are used to calculate the molecular weights of proteins of interest run in successive channels. In some embodiments, the reference sample is run with a protein quantitation standard as described herein. The sample containing the target protein of interest is separated in a different channel. The mass of the target protein can then be determined using the mass standard curve generated from the protein quantitation standard. In some embodiments, a known quantity of a reference protein is added to the sample containing the target protein, and the mass standard curve can be used in conjunction with the sample's reference protein (as a normalizing factor) to more accurately determine the target protein's mass.

A. Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Thus, in one embodiment, a computer implemented method is provided for determining the mass quantity of a target polypeptide. In one embodiment, the computer implemented method comprises, under the control of one or more computer systems configured with executable instructions, the steps of:

i. determining that a protein quantitation standard is present in a gel image;
  ii. identifying the quantitation polypeptide bands in the standard;
  iii. quantifying the quantitation polypeptide bands in the standard;
  iv. generating a linear or non-linear regression fit, for example, an intensity versus mass calibration curve; and
  v. calculating the target proteins mass quantity from the regression fit; and
  vi. providing the calculated mass quantity.

In some embodiments, the computer implemented method is implemented by a computer system that is in electronic communication with an image scanner that is capable of detecting the bands in a gel or image of a gel. The computer implemented method can determine the mass quantity of a target protein that is loaded into one lane of a gel based on quantifying the polypeptide bands in another lane of the gel. In some embodiments, the computer implemented method determines the standard curve using point-to-point semi-log, or regression analysis of Elder-Southern, Logistic, Linear, Quadratic, Cubic or Cubic Spline functions.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein. In some embodiments, the computer product comprises a non-transitory computer readable medium storing a plurality of instructions for controlling a processor to perform an operation of one or more of the following steps:

i. determining that a protein quantitation standard is present in a gel image;
  ii. identifying the quantitation polypeptide bands in the standard;
  iii. quantifying the quantitation polypeptide bands in the standard;
  iv. generating a linear or non-linear regression fit, for example, an intensity versus mass calibration curve; and
  v. calculating the target proteins mass quantity from the regression fit; and
  vi. providing the calculated mass quantity.

In some embodiments, the computer product comprises a non-transitory computer readable medium storing a plurality of instructions for controlling a processor to perform an operation of one or more of the following steps:

(i) receiving data comprising the quantity of the unstained polypeptides in a protein quantitation standard, the protein quantitation standard comprising a set of unstained polypeptides having different electrophoretic mobilities present in different quantities;
  (ii) generating a regression fit based on the data received;
  (iii) calculating the target polypeptide's mass from the regression fit; and
  (iv) providing the calculated mass.

In some embodiments, a system is provided, the system comprising the computer product described above, and one or more processors for executing instructions stored on the computer readable medium.

Figure 4:
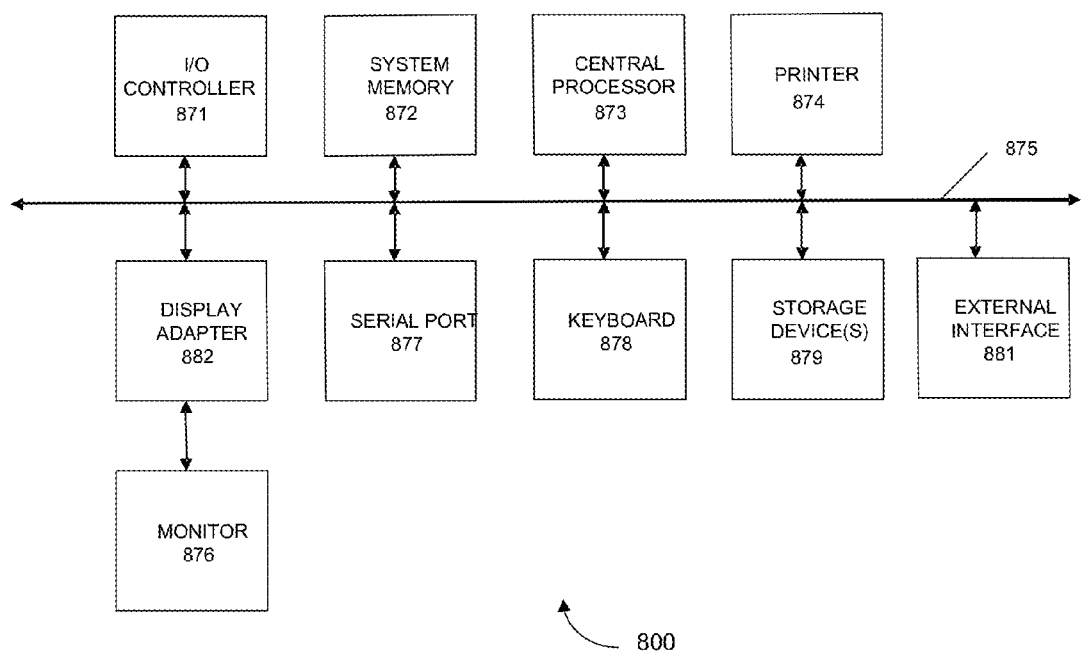
FIG. 4 shows a block diagram of an example computer system 800 usable with the system and methods according to embodiments described herein.

FIG. 4 shows a block diagram of an example computer system 800 usable with system and methods according to embodiments of the present disclosure.

Any of the computer systems mentioned herein may utilize any suitable number of subsystems. Examples of such subsystems are shown in FIG. 4 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 4 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

III. Kits

The disclosure also provides kits containing the protein quantitation standard described herein. For example, the kit can provide a container comprising a set of prestained polypeptides and a set of unstained polypeptides, where each of the prestained polypeptides have different molecular weights and each of the unstained polypeptides are provided in different amounts for a given molecular weight. The kit can also provide each prestained polypeptide having the same molecular weight in a separate container, and each unstained polypeptide having the same molecular weight in a separate container. This would allow the user to combine the prestained and unstained polypeptide into a mixture as desired. The kit can also provide additional reagents for detecting and quantifying the polypeptides of the standard, and instructions for using the kit.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A protein quantification standard that can be loaded into one lane of an electrophoresis gel, said standard comprising a mixture of
   (i) a set of unstained polypeptides, wherein members of the set of unstained polypeptides have different electrophoretic mobilities and are present in different quantities, and
   (ii) a set of prestained polypeptides having different electrophoretic mobilities,
   such that the standard is suitable for generating a protein mass standard curve and a molecular weight ladder from one lane of a gel.

2. The protein quantification standard of claim 1, wherein the polypeptides range in size from about 2 kDa to about 250 kDa.

3. The protein quantification standard of claim 1, wherein members of the set of prestained polypeptides have different electrophoretic mobilities.

4. The protein quantification standard of claim 1, wherein members of the set of prestained polypeptides are present in similar quantities.

5. The protein quantification standard of claim 1, wherein at least one prestained polypeptide and at least one unstained polypeptide have different electrophoretic mobilities.

6. The protein quantification standard of claim 1, wherein the unstained polypeptides comprise an affinity tag.

7. The protein quantification standard of claim 1, wherein the unstained polypeptides comprise a detection tag.

8. The protein quantification standard of claim 1, wherein the unstained polypeptides comprise substantially similar percentages of tryptophan.

9. The protein quantification standard of claim 1, wherein the prestained polypeptides are stained with one or more colored dyes, wherein the one or more colored dyes comprise a single color dye, a combination of different colored dyes, or fluorescent dyes.

10. The protein quantification standard of claim 1, further comprising an unstained polypeptide that is identical in amino acid sequence to a prestained polypeptide.

11. A kit comprising the protein quantification standard of claim 1.

12. A method for determining the mass quantity of a target polypeptide, comprising:
    electrophoretically migrating the target polypeptide in one lane of a gel and the protein quantitation standard of claim 1 in another lane of the gel;
    detecting the target polypeptide and the protein quantitation standard;
    comparing the detected amount of the target polypeptide to a mass standard curve generated from the protein quantitation standard to thereby determine the mass quantity of the target polypeptide.

13. The method of claim 12, further comprising detecting prestained polypeptide bands of a protein standard to determine the apparent molecular weight of the target protein.

14. The method of claim 12, wherein the detecting comprises stain-free imaging.

15. The method of claim 12, wherein the detecting comprises fluorescence imaging.

16. The method of claim 12, wherein the detecting comprises contacting the unstained polypeptides with a stain or dye and visualizing the polypeptides.

17. The method of claim 12, further comprising contacting the unstained polypeptides with one or more ligands that specifically bind the polypeptides of the standard.

18. The method of claim 12, wherein the target polypeptide and the protein quantitation standard are eletrophoretically migrated in a microfluidic instrument.

19. The method of claim 12, further comprising:
    under the control of one or more computer systems configured with executable instructions;
    quantifying the unstained polypeptides in the protein quantitation standard;
    generating a regression fit based on the quantifying step;
    calculating the target polypeptide's mass from the regression fit; and
    providing the calculated mass.

20. The protein quantification standard of claim 9, wherein at least one of the one or more dyes is visible to the human eye.

* * * * *